US00PP11476P

United States Patent [19]

van Andel

[11] Patent Number: Plant 11,476

[45] Date of Patent: Aug. 8, 2000

[54] SPATHIPHYLLUM PLANT NAMED 'CEASAR'

[75] Inventor: Otto Jan Robert van Andel, Kudelstaart, Netherlands

[73] Assignee: Gebr. Braam, de Kwakel, Netherlands

[21] Appl. No.: 09/106,024

[22] Filed: Jun. 29, 1998

[51] Int. Cl.[7] ..... A01H 5/00

[52] U.S. Cl. ..... Plt./364

[58] Field of Search ..... Plt./364

[56] References Cited

U.S. PATENT DOCUMENTS

P.P. 6,144 4/1988 Caldwell ..... Plt./364

P.P. 8,844 7/1994 Van Dordrecht ..... Plt./364

OTHER PUBLICATIONS

Huxley, Anthony, ed. *The New Royal Horticultural Society Dictionary of Gardening*. vol. 4 The Stockton Press NY p345, Jul. 1992.

*Primary Examiner*—Howard J. Locker
*Assistant Examiner*—Wendy A. Baker
*Attorney, Agent, or Firm*—C. A. Whealy

[57] ABSTRACT

A distinct cultivar of Spathiphyllum plant named 'Ceasar', characterized by its tall, upright plants; large leaves that are held upright to horizontal to the petiole; moderate to high vigor and moderate growth rate; numerous large white spathes that are positioned above the foliage on strong and erect peduncles; and long-lasting inflorescences.

4 Drawing Sheets

BACKGROUND OF THE INVENTION

The present invention relates to a new and distinct cultivar of Spathiphyllum plant, botanically known as Spathiphyllum, and hereinafter referred to by the cultivar name 'Ceasar'.

The new cultivar is a product of a planned and controlled breeding program conducted by the Inventor in De Kwakel, The Netherlands. The objective of the breeding program is to create new Spathiphyllum cultivars with good plant habit and attractive leaf and flower colors.

The new cultivar originated from a cross by the Inventor between the Spathiphyllum cultivar 'Ceres' (disclosed in U.S. Plant Pat. No. 8,844) and an unnamed selection of *Spathiphyllum cochlearispathum* as the male or pollen parent. The cultivar 'Ceasar' was discovered and selected by the Inventor in May, 1995 as a plant within the progeny of the stated cross in a controlled environment in De Kwakel, The Netherlands.

In side-by-side comparisons conducted by the Inventor in De Kwakel, The Netherlands, the following differences between the new Spathiphyllum and the female parent, the cultivar 'Ceres', have been observed:

1. Plants of the new Spathiphyllum are taller than plants of the cultivar 'Ceres'.

2. Plants of the new Spathiphyllum are more open than plants of the cultivar 'Ceres'.

3. Leaves of plants of the new Spathiphyllum are lighter green and larger than leaves of plants of the cultivar 'Ceres'.

4. Spathes of plants of the new Spathiphyllum are larger but not as white as spathes of plants of the cultivar 'Ceres'.

In side-by-side comparisons conducted by the Inventor in De Kwakel, The Netherlands, the following differences between the new Spathiphyllum and the male parent, an unnamed selection of *Spathiphyllum cochlearispathum*, have been observed:

1. Plants of the new Spathiphyllum are shorter than plants of the unnamed selection of *Spathiphyllum cochlearispathum.*

2. Plants of the new Spathiphyllum are denser than plants of the unnamed selection of *Spathiphyllum cochlearispathum.*

3. Leaves of plants of the new Spathiphyllum are lighter green, less glossy, longer and more narrow than leaves of plants of the unnamed selection of *Spathiphyllum cochlearispathum.*

4. Spathes of plants of the new Spathiphyllum are white whereas spathes of plants of the unnamed selection of *Spathiphyllum cochlearispathum* are green in color.

Asexual propagation by divisions and tissue-culture of the new cultivar at De Kwakel, The Netherlands, has shown that the unique features of this new Spathiphyllum plant are stable and reproduced true to type in successive generations of asexual propagation.

BRIEF SUMMARY OF THE INVENTION

The new Spathiphyllum has not been observed under all possible environmental conditions. The phenotype may vary somewhat with variations in environment such as temperature and light intensity, without, however, any variance in genotype.

The following traits have been repeatedly observed and are determined to be the unique characteristics of 'Ceasar'. These characteristics in combination distinguish 'Ceasar' as a new and distinct cultivar:

1. Tall, upright plants.

2. Large leaves that are held upright to horizontal to the petiole.

3. Moderate to high vigor and moderate growth rate.

4. Numerous large white spathes that are positioned above the foliage on strong and erect peduncles.

5. Long-lasting infloresences.

Plants of the new Spathiphyllum can be compared to plants of the commercial Spathiphyllum cultivar 'Sensation' (not patented). In side-by-side comparisons conducted by the Inventor in De Kwakel, The Netherlands, the following differences between the new Spathiphyllum and the cultivar 'Sensation' have been observed:

1. Plants of the new Spathiphyllum are shorter than plants of the cultivar 'Sensation'.

2. Plants of the new Spathiphyllum considerably denser than plants of the cultivar 'Sensation'.

3. Leaves of plants of the new Spathiphyllum are lighter green and less glossy than leaves of plants of the cultivar 'Sensation'.

4. Spathes of plants of the new Spathiphyllum are smaller and not as white as spathes of plants of the cultivar 'Sensation'.

5. Plants of the new Spathiphyllum flower earlier than plants of the cultivar 'Sensation'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Spathiphyllum.

The photograph on the first sheet comprises a top perspective view of a typical potted plant of 'Ceasar'.

The photograph on the second sheet comprises a close-up view of the upper surface of a typical leaf of 'Ceasar'.

The photograph on the third sheet comprises a close-up view of a typical spathe and spadix of 'Ceasar'.

The photograph on the fourth sheet comprises a close-up view of the back of a typical spathe of 'Ceasar'. Spathe and leaf colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in De Kwakel, The Netherlands, in a glass greenhouse under typical commercial conditions with day and night temperatures averaging 22 and 19° C., respectively, and light levels of about 22,000 to 28,000 lux.

Botanical classification: Spathiphyllum cultivar 'Ceasar'.

Parentage:

*Female parent.*—Spathiphyllum cultivar 'Ceres' (disclosed in U.S. Plant Pat. No. 8,844).

*Male parent.*—Unnamed selection of *Spathiphyllum cochlearispathum.*

Propagation: By division or by tissue culture.

*Time to initiate roots.*—About 15 days at 23° C.

*Rooting habit.*—Freely branching, numerous fleshy roots.

Plant description:

*Plant shape.*—Upright, inverted triangle, symmetrical.

*Growth habit.*—Erect when young, becoming more outwardly arching as leaves develop. Appropriate for 17 to 25-cm containers.

*Plant height.*—About 65 cm from soil level to top of leaf plane.

*Plant vigor.*—Moderate to high vigor and moderate growth rate.

*Time to finishing.*—About 14 months are required to produce a finished 17-cm plant with two flowering stems from a tissue-cultured plantlet.

*Foliage description.*—Quantity of leaves: About 38. Shape: Lanceolate, somewhat convex. Aspect: Mature leaves held upright to perpendicular to petiole. Length: About 40 cm. Width: About 19 cm. Apex: Apiculate, apex is recurved. Base: Cuneate. Margin: Entire, slightly undulating. Texture: Glabrous and slightly glossy, veins slightly sunken. Color: Young, upper surface: Close to 144A. Young, lower surface: Close to 138B to 138C. Mature, upper surface: Close to 137B to 137C. Mature, lower surface: Close to 138A to 138B. Venation, upper surface: Midvein same color as leaf surface, lateral veins, close to 144A. Venation, lower surface: Midvein same color as leaf surface, lateral veins, close to 144B. Petiole length: About 27 cm. Petiole color: 138A. Geniculum lenght: About 2.25 cm. Geniculum diameter: About 6 mm. Geniculum angle: Straight. Geniculum color: 138B.

Inflorescence description:

*Inflorescence arrangement.*—Large concave spathes with spadices held above the foliage. Numerous inflorescences arise from leaf axils. Flowering continuous. Inflorescences persistent.

*Inflorescence longevity.*—Inflorescences are long-lasting, generally maintaining white color for about six weeks on the plant depending on light and temperature levels.

*Spathe.*—Appearance: Leathery. Angle: Erect, upright. Shape: Lanceolate. Apex: Apiculate; elongated apex cirrhous. Base: Cuneate. Margin: Entire. Length: About 23 cm. Width: About 10 cm. Aspect: Concave, curving towards the spadix. Color, fully opened spathes: Front surface: 157A to 157B. Back surface: 157A with green, 137D to 144A, midvein.

*Spadix.*—Axis: Longitudinal. Cross section: Rounded. Length: About 8 cm. Diameter: About 1 cm. Color: 158D.

*Flowers.*—Quantity per spadix: About 180. Shape: Conical. Size: About 2 mm. Stigma shape: Rounded. Pollen color: Mature: 158D. After senescence: 159A.

*Peduncle.*—Aspect: Strong and erect. Length: About 55 cm. Color: 138A.

Disease resistance: No known Spathiphyllum diseases observed to date on plants grown under commercial greenhouse conditions. Resistance to known Spathiphyllum diseases has not been observed.

Seed development: Seed development has not been observed.

It is claimed:

1. A new and distinct cultivar of Spathiphyllum plant named 'Ceasar', as illustrated and described.

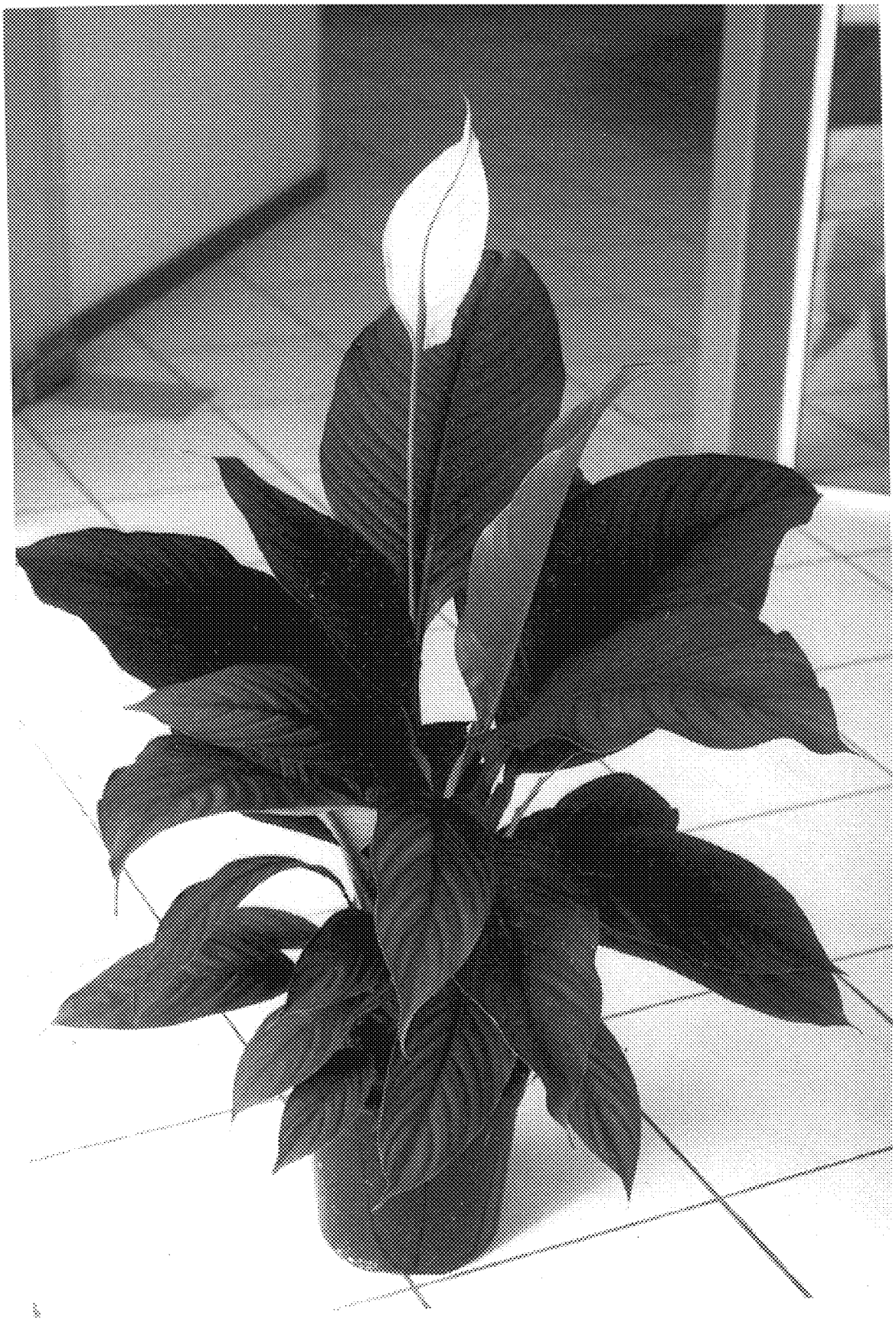

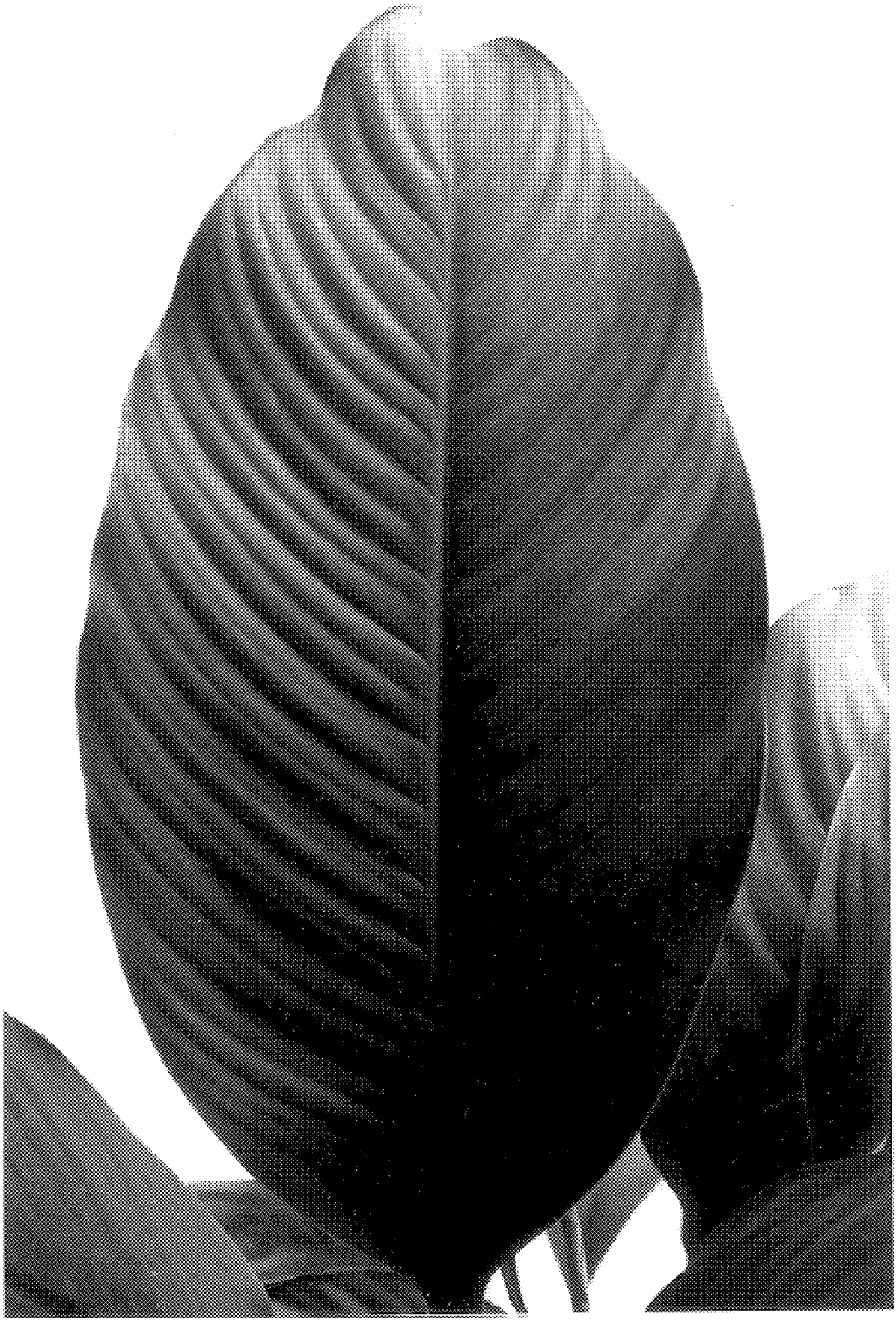

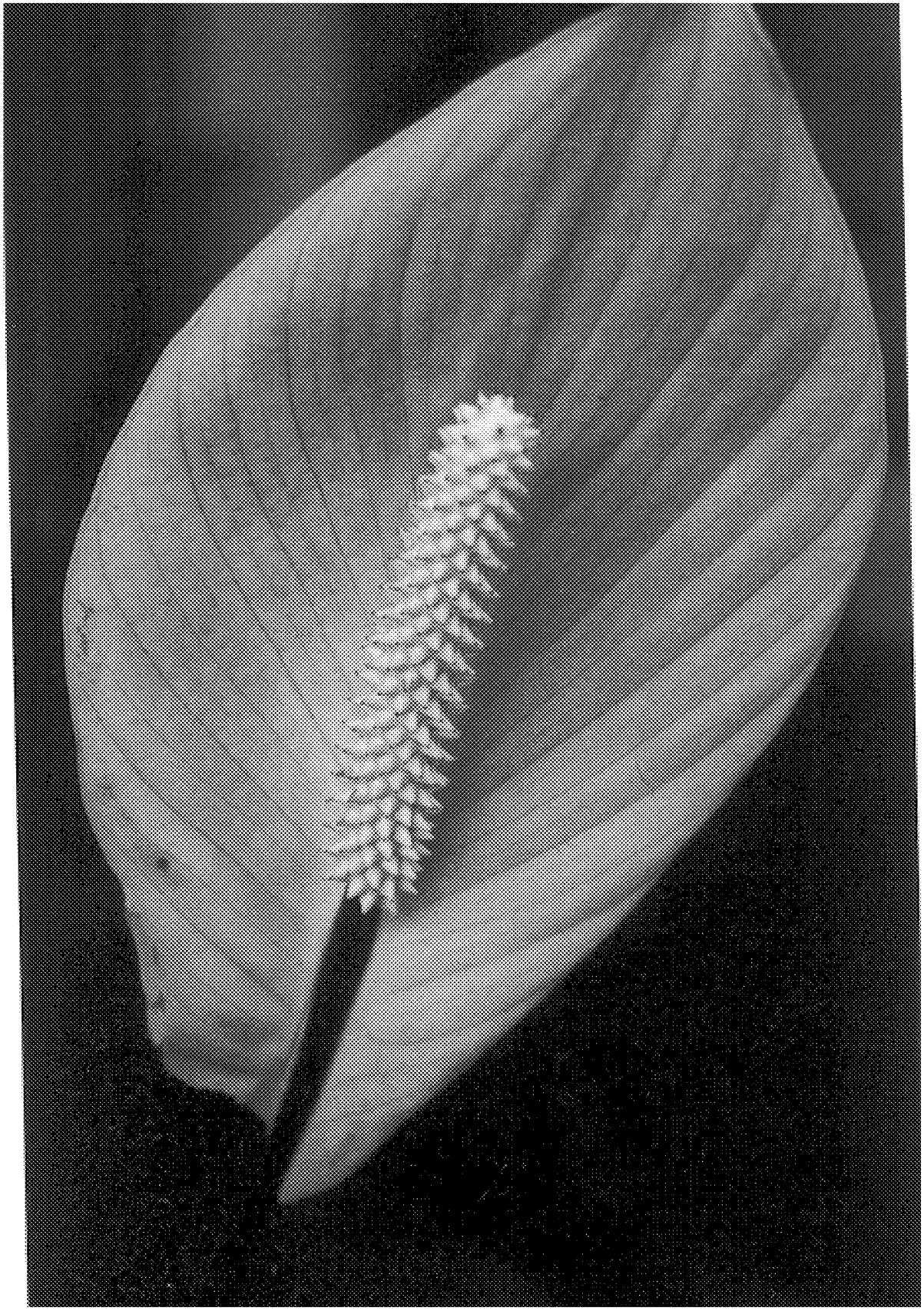

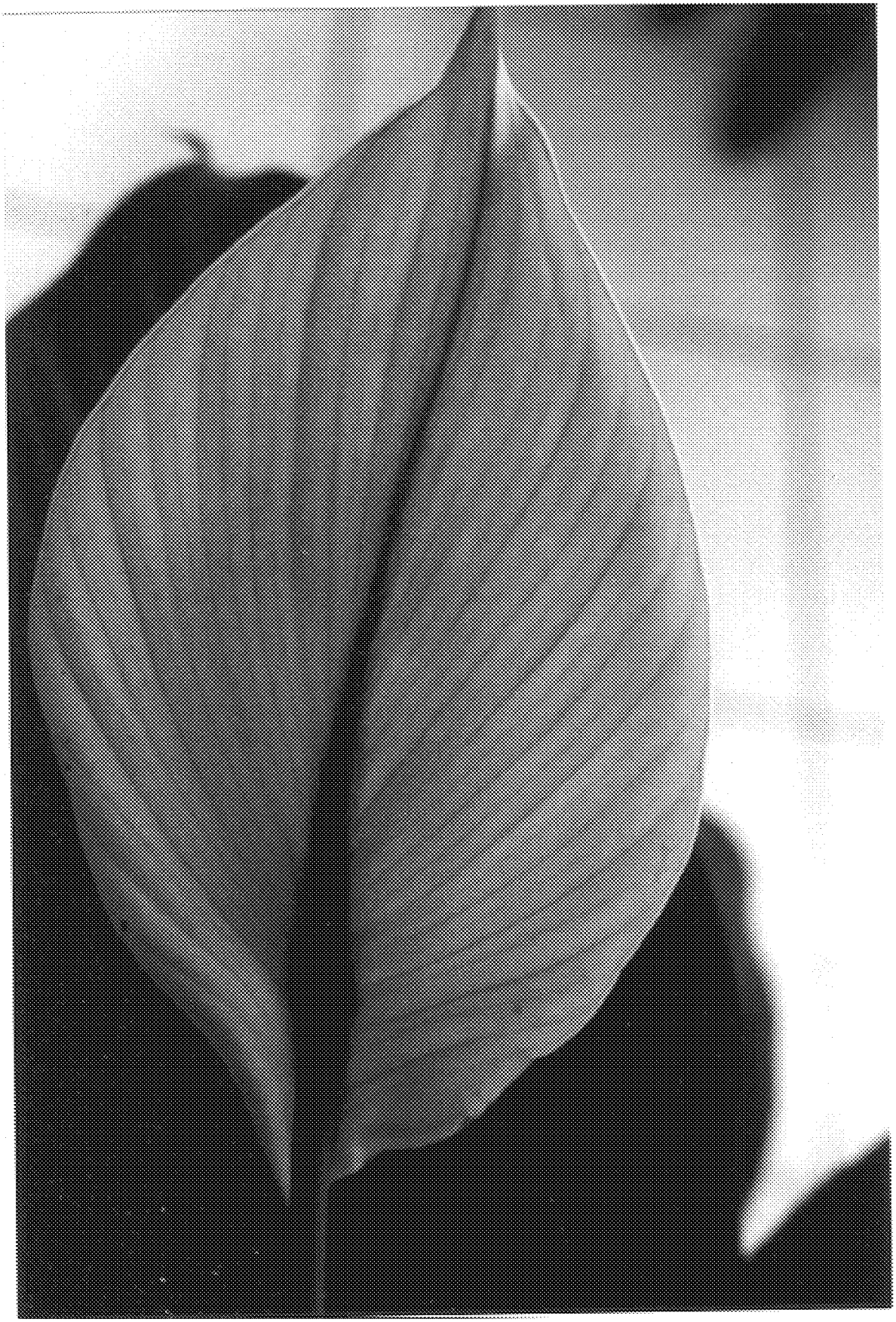

* * * * *